(12) United States Patent
Lee et al.

(10) Patent No.: US 8,353,919 B2
(45) Date of Patent: Jan. 15, 2013

(54) WOUND CLOSURE ASSISTING AND MAINTAINING APPARATUS

(75) Inventors: Eui Tai Lee, Seoul (KR); Hee Chan Kim, Seoul (KR); Hwa Ryoung Kim, Seoul (KR)

(73) Assignee: LEE, Eui Tai, Seoul (KR)

( * ) Notice: Subject to any disclaimer, the term of this patent is extended or adjusted under 35 U.S.C. 154(b) by 1082 days.

(21) Appl. No.: 10/562,483

(22) PCT Filed: Jun. 25, 2004

(86) PCT No.: PCT/KR2004/001545
§ 371 (c)(1),
(2), (4) Date: Jan. 23, 2007

(87) PCT Pub. No.: WO2004/112617
PCT Pub. Date: Dec. 29, 2004

(65) Prior Publication Data
US 2008/0027484 A1    Jan. 31, 2008

(30) Foreign Application Priority Data
Jun. 26, 2003  (KR) .................. 10-2003-0042017

(51) Int. Cl.
*A61B 17/10* (2006.01)
(52) U.S. Cl. ...................................................... 606/139
(58) Field of Classification Search .......... 606/213–218, 606/139, 148, 232, 144–146, 150, 224, 225, 606/191, 194; 604/57–64, 104–111, 208–211, 604/220–224, 227, 228, 230, 233, 241, 15, 604/206
See application file for complete search history.

(56) References Cited

U.S. PATENT DOCUMENTS

| | | | | |
|---|---|---|---|---|
| 4,583,974 A | * | 4/1986 | Kokernak | 604/211 |
| 4,723,938 A | * | 2/1988 | Goodin et al. | 604/97.02 |
| 4,890,612 A | * | 1/1990 | Kensey | 606/213 |
| 4,906,231 A | * | 3/1990 | Young | 604/110 |
| 5,021,059 A | * | 6/1991 | Kensey et al. | 606/213 |
| 5,190,526 A | * | 3/1993 | Murray et al. | 604/110 |
| 5,391,182 A | * | 2/1995 | Chin | 606/213 |
| 5,478,353 A | * | 12/1995 | Yoon | 606/213 |

(Continued)

OTHER PUBLICATIONS

International Search Report for application No. PCT/KR2004/001545.

*Primary Examiner* — Kathleen Sonnett
*Assistant Examiner* — Jocelin Tanner
(74) *Attorney, Agent, or Firm* — Lowe Hauptman Ham & Berner, LLP

(57) ABSTRACT

Provided is a wound closure assisting and maintaining apparatus that can be attached to a wide open wound of a patient and can stretch skin around the wound gradually to achieve the wound closure and maintain the wound closure during most critical postoperative period. The apparatus includes: a loop suture being threaded through skin; a tightening member for gathering both ends of the threaded loop suture at one point and for exerting a pressure of wound tightening force evenly on skin; a pulling member for pulling the loop suture in order to tighten the threaded loop suture; a housing member for housing the pulling member and making the loop suture tightened by transformation of a pulling force to a wound tightening force when pulling member pulls the loop suture out of skin; and a locking member for fixing a position of the pulling member to maintain the tightened status.

16 Claims, 3 Drawing Sheets

U.S. PATENT DOCUMENTS

| | | |
|---|---|---|
| 5,478,354 A | 12/1995 | Tovey et al. |
| 5,486,196 A | 1/1996 | Hirshowitz et al. |
| 5,549,633 A * | 8/1996 | Evans et al. .................. 606/139 |
| 5,649,959 A * | 7/1997 | Hannam et al. ............... 606/213 |
| 5,759,193 A | 6/1998 | Burbank et al. |
| 5,947,983 A | 9/1999 | Solar et al. |
| 6,120,525 A | 9/2000 | Westcott |
| 6,206,895 B1 | 3/2001 | Levinson |
| 6,221,084 B1 * | 4/2001 | Fleenor ......................... 606/148 |
| 6,355,050 B1 * | 3/2002 | Andreas et al. ................ 606/144 |
| 6,471,715 B1 | 10/2002 | Weiss |
| 6,524,326 B1 | 2/2003 | Zhu et al. |
| 6,860,895 B1 * | 3/2005 | Akerfeldt et al. ............. 606/215 |
| 7,048,755 B2 * | 5/2006 | Bonutti et al. ................ 606/232 |

* cited by examiner

WOUND CLOSURE ASSISTING AND MAINTAINING APPARATUS

CROSS REFERENCE TO RELATED APPLICATION

This application is the National Phase application of International Application No. PCT/KR2004/001545, filed Jun. 25, 2004, which designates the United States and was published in English. This application, in its entirety, is incorporated herein by reference.

TECHNICAL FIELD

The present invention relates to a wound closure assisting and maintaining apparatus for closing an open wound; and more particularly, a wound closure assisting and maintaining apparatus for maintaining closure of an open wound during the critical immediate postoperative period after a surgical operation by protecting the closed wound from forces of body position changes and daily activities.

BACKGROUND ART

In case of a wide open wound caused by an accident, a disease or an operation, the entire wound may not be securely sutured at one time. If the wide open wound is sutured at once, the wound may be easily disrupted by little impact or the skin around the wound may be dead due to excessive strain loaded on it. To close those wounds successfully, a doctor should clean the wide open wound by removal of dead tissue and he may need the suturing to be tightened at several stages using a wound closure assisting apparatus. Then, the area of the wound can be made smaller by gradual tightening in the middle of, and/or after the operation.

Meanwhile, a bedsore may arise around the skin over protruding bones of patient who spends most of a day lying on a bed. In order to treat the bedsore, the patient should be deeply anesthetized with general endotracheal anesthesia or spinal anesthesia for a major surgery and he should be lying prone more than three weeks, ideally.

But those patients who have suffered bedsore are usually so severely debilitated physically and/or mentally that they are not able to move their position by themselves. In addition to poor general condition, they may have some serious underlying diseases such as cancer, paraplegia, malnutrition, dementia, and so on. Thus, they can not tolerate general anesthesia, spinal anesthesia, and major surgery, nor they can even maintain prone position for an extended period. Furthermore, if a patient has a neurological problem, he may develop involuntary contraction intermittently. The involuntary contraction or pressure caused by the patient's own body weight contrasts with the ideal conditions for wound healing and, eventually, results in inability to repair the bedsore or breakup of the repair with poor general, mental, and neurologic conditions of the patient.

Similarly, if a wide open wound is located on a human part with frequent movement, such as joints, face, body and limbs, the part should be fixed with a splint or a cast for a long period after repair of the wound. Otherwise, the repaired wound may be torn apart or widened to leave a big scar. However, such a long period of cast or splint makes the casted or splinted joint stiff in old patients. In addition, a woman usually hates the large scar left on her skin.

To overcome above mentioned problems for skin shortage, condition, position and activities of the patient in treatment of the wide open wound, a conventional wound closure assisting apparatus has been introduced. The conventional wound closure assisting apparatus is applied at margins of the wide open wound in order to stretch skin around the wound gradually and to help close the wound. It is a great help for those who have some wide open wounds. But conventional apparatus is not devised for long-term use in patient's body.

Hereinafter, the conventional wound closure assisting apparatus will be described with reference to FIGS. 1 to 3. FIG. 1 is a perspective view illustrating a conventional wound closure assisting apparatus, and FIGS. 2A and 2B are side sectional views depicting a process using the conventional wound closure assisting apparatus.

Referring to FIG. 1, the conventional wound closure assisting apparatus includes a pair of threading pins 30, a distance controlling bar 10, a supporting member 21, and a space controlling member 20.

The threading pins 30 are set running through the skin at the vicinity of wide open wound parallel to each other. The distance controlling bar 10 is applied parallel to skin surface and vertical to the threading pins 30 with attached space controlling member 20 to support one of the threading pins 30. The supporting member 21 is settled at one end of the distance controlling bar 10 and supports the other threading pin 30. The space controlling member 20 at the other end of the distance controlling bar 10 can rotate and advance the attached distance controlling bar 10 through a hole in supporting member 21 by turning a knob. So, one can adjusts the space between the threading pins 30 by turning a knob on the space controlling member 20.

Referring to FIGS. 2 and 3, the two threading pins 30 are set parallel to each other, penetrating skin at the vicinity of a wide open wound 1, and the supporting member 21 and the space controlling member 20 at both ends of the distance controlling bar 10 are positioned on the external sides of the suturing pins 30. If the knob on the space controlling member 20 is turned, the space controlling member 20 is moved toward to the supporting member 21, as shown in FIG. 2. Then, the width of the wide open wound 1 is narrowed and ready for closure by suturing, which is shown in FIG. 3.

However, the conventional wound closure assisting apparatus has shortcomings that the full set of distance controlling bar 10, the suturing pins 30, the supporting member 21, and the space controlling member 20 should be hard, rigid, heavy, complex and bulky to support each other. Therefore, the conventional apparatus has severe limitation of application during the operation in three-dimensional human body. Although it can be used in a flat and wide part of body with little movement, it can not be set in a narrow, convex, concave or uneven area. Also, it can not be used when the wound shape is round or polygonal rather than linear or elliptical. The conventional device has even more serious disadvantages in duration of application after the operation. It can not be maintained on weight bearing area because if the wound closure assisting apparatus is pressed down, it will press the skin to result in device failure or ulcer and wound disruption of human body. It is not maintainable around the mobile joint areas without help of cast or splint. But with cast or splint, the activities of the patient are restricted and the dressing and examination of the wound will be much more difficult each time and joint stiffness can be a serious long-term problem especially in elderly. Moreover, since it is detached from the threading pins easily, it can not be maintained for a long time if the patient moves his body part in daily activities or if the position of the patient needs to be changed to prevent bed sore. The conventional apparatus is not likely to maintain its position both in ambulatory patient and bed ridden patient. Even if it is able to maintain its position for a short period of time, the patient will experience feelings of discomfort and insecurity and the compliance of the patient will be low.

In addition, since it uses only a pair of threading pins to assist the closure of the wide open wound, the skin penetrated by the threading pins suffers excessive strain and thus the closure is sometimes performed ineffectively.

DISCLOSURE OF INVENTION

Technical Solution

It is, therefore, an object of the present invention to provide a wound closure assisting and maintaining apparatus for maintaining the wound closure during a long period of medical treatment because of the softness, flexibility and impact absorbing property of this apparatus.

It is another object of the present invention to provide a wound closure assisting and maintaining apparatus for effectively closing an open wound and maintaining a closure of the open wound without being influenced by movement, posture and affected part of a patient.

It is another object of the present invention to provide a wound closure assisting and maintaining apparatus made of soft and light material in order to make a patient comfortable even on long-term application of the wound closure assisting and maintaining apparatus.

It is still another object of the present invention to provide a wound closure assisting and maintaining apparatus which can be used in wounds with any surfaces and any shapes such as narrow, wide, flat, convex, concave, and uneven surfaces and linear, elliptical, round and polygonal shapes.

It is further still another object of the present invention to provide a wound closure assisting and maintaining apparatus to avoid too much loading of extensive strain on a particular area of the wide open wound by even distribution of tension along the passage of the suture.

In accordance with one aspect of the present invention, there is provided a wound closure assisting and maintaining apparatus including: a loop suture being threaded through skin as an elongated circle across both margins of a wide open wound; a tightening member for gathering both ends of the threaded loop suture at one point in order to tighten the threaded loop suture and for exerting a pressure of wound tightening force evenly on skin; a pulling member for pulling the loop suture in order to tighten the threaded loop suture; a housing member for housing the pulling member and making the loop suture tightened by transformation of a pulling force to a wound tightening force when pulling member pulls the loop suture out of skin; and a locking member for fixing a position of the pulling member in relation to the housing member constant by making movement of the pulling member in one-way to maintain the tightened status.

The housing member is made of soft elastic material and the pulling member is made of hard rigid material in order to absorb impacts of positional changes and daily activities of the patient by the difference in flexibility. The housing member may have a ruler scale on it to measure the length of pulling.

It is desirable to form saw teeth on inside surface of the locking member and another saw teeth on outside surface of the pulling member in order to lock the pulling member by engaging two sets of saw teeth after pulling desired length. The pulling member may have a ruler scale on it to measure the length of pulling.

It is also desirable to include a strain gauging unit in the wound closure assisting and maintaining apparatus for safe wound tightening to prevent skin death due to too much strain of wound tightening. Here, a strain gauge, an optical sensor and other devices for measurement of strain can be used as the strain gauging unit.

Desirably, the wound closure assisting and maintaining apparatus may further include a buffering unit which absorbs the extra strain loaded on the loop suture by the movement of patient or any impact on the patient. The strain gauging unit may be simply formed by an elastic member. In other words, the elastic member can be used to measure the strain and also to buffer the strain. The strain loaded on the loop suture can be measured by the extension of the elastic member. The device has two more inherent buffering mechanisms other than the elastic member, that is, the partial mobility in the middle of the dressing and the relative softness of the flexible housing member as compared with the rigid pulling member.

The wound closure assisting and maintaining apparatus of the present invention can be maintained in areas of much movement, such as a joint. The wound closure assisting and maintaining apparatus prevents rupture of the repaired wound around joint areas because it absorbs the change of strain caused by movement and it maintains a regular strain on the wound by above-mentioned three buffering mechanisms. The strain gauging unit or the buffering unit may be formed by an elastic member connected to the loop suture or inserted in the middle of the housing member or pulling member. The elastic member may be a coil spring.

It is desirable to further include in the wound closure assisting and maintaining apparatus a loosening unit for releasing too severely tightened loop suture by adjustment of the position of pulling member. The loosening unit includes a screw opening formed at one end of the housing member; and a bolt for loosening of the pulling member, which is formed in the locking member.

The loosening unit may include a cover with a saw tooth on inside surface, and the saw tooth is engaged or disengaged with another saw tooth on outer surface of the pulling member by closing or opening the cover in order to adjust the position of pulling member.

And more simply, if the housing member is made of soft material as described above, one can get the loosening effect by trimming the skin-side end of housing member and resultant shortening of the housing member.

The wound closure assisting and maintaining apparatus may include a winding screw and a separate or attached winding screw handle for winding of the pulling member in order to pull the loop suture. In that case, length of the device can be shortened and thus, better feeling and compliance of the patient will be expected

BRIEF DESCRIPTION OF THE DRAWINGS

The above and other objects and features of the present invention will become better understood with regard to the following description of the preferred embodiments given in conjunction with the accompanying drawings, in which.

MODE FOR THE INVENTION

Hereinafter, a wound closure assisting and maintaining apparatus in accordance with a preferred embodiment of the present invention will be described in detail with reference to the accompanying drawings.

Figure 4:
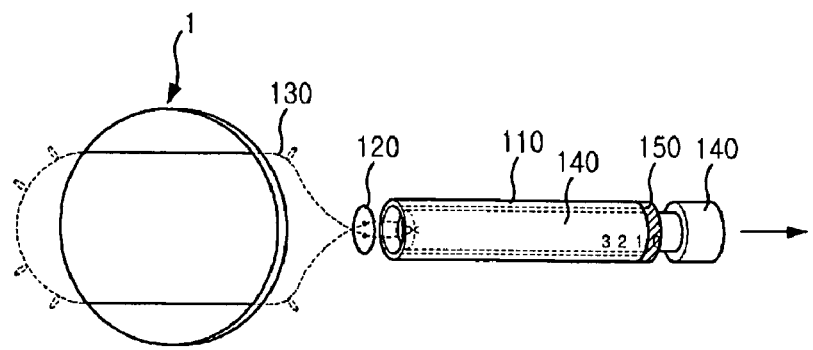
FIGS. 4 and 5 are plane views describing a wound closure assisting and maintaining apparatus in accordance with an embodiment of the present invention.
Figure 5:
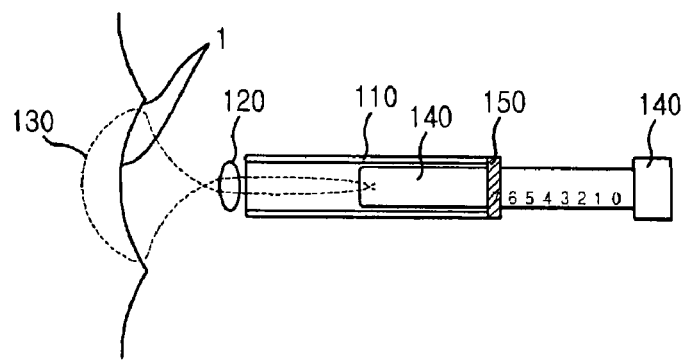

FIGS. 4 and 5 are plane views describing a wound closure assisting and maintaining apparatus in accordance with an embodiment of the present invention.

Referring to FIGS. 4 and 5, the wound closure assisting and maintaining apparatus includes: a loop suture 130, a tightening member 120, a pulling member 140, a housing member 110, and a locking member 150.

The loop suture 130 is threaded circularly through skin on both side of the wide open wound. Two ends of the loop suture 130 are tied to the pulling member 140 after passing out of skin and through the tightening member 120. The tightening member is a round flat disc with two holes. Each end of the loop suture 130 is passed through the corresponding hole to be tied and secured to one end of the pulling member 140. The tightening member 120 provides a base for pulling of loop suture and tightening of wound, and which disperses the pressure of wound tightening force evenly on skin. The pulling member 140 pulls the loop suture 130 in order to tighten the wide open wound. The pulling member 140 can be manufactured by various materials with various shapes. However, in the preferred embodiment, it is manufactured as a long flat strip made of hard rigid plastic with saw teeth on one surface of the flat plastic strip.

The housing member 110 has a form of hollow cylinder and houses the pulling member 140. The tightening member 120 is installed at one end of the housing member 110. The housing member transforms the pulling force on loop suture 130 to tightening force on wound by action-reaction mechanism when pulling member 140 pulls the loop suture 130 out of skin. The locking member 150 fixes the position of pulling member 140 in relation to the housing member 110 to maintain tightening of the wound. That is, the locking member 150 has a locking mechanism between the pulling member 140 and the locking member 150 allows the pulling member 140 to move through it only in one-way. So, the locking member 150 can fix the position of the pulling member 140 after pulling it as much length as needed to tighten the wide open wound. In this embodiment, the locking member 150 has saw teeth on inside surface of it. The saw teeth of the pulling member 140 has a reverse form compared to its counterpart on the locking member 150. Therefore, the pulling member 140 can be pulled only in one direction and it is not allowed to move in the opposite direction because the saw teeth on the pulling member 140 and the other saw teeth on the locking member 150 are engaged each other in interlocking position after the pulling member 140 is pulled for a required length.

It is desirable to make the housing member 110 from soft elastic material so that a patient could use the wound closure assisting and maintaining apparatus comfortably during the period of medical treatment.

Also, a ruler scale may be marked on one side of the housing member 110 or the pulling member 140. Then, since the position of pulling member 140 can be known, length of the pulled loop suture can be measured.

The tightened wound by pulling of loop suture will not loose since the pulling member 140 can be moved only in pulling direction. It is because of the one-way locking mechanism between the locking member 150 and the pulling member 140.

Figure 1:
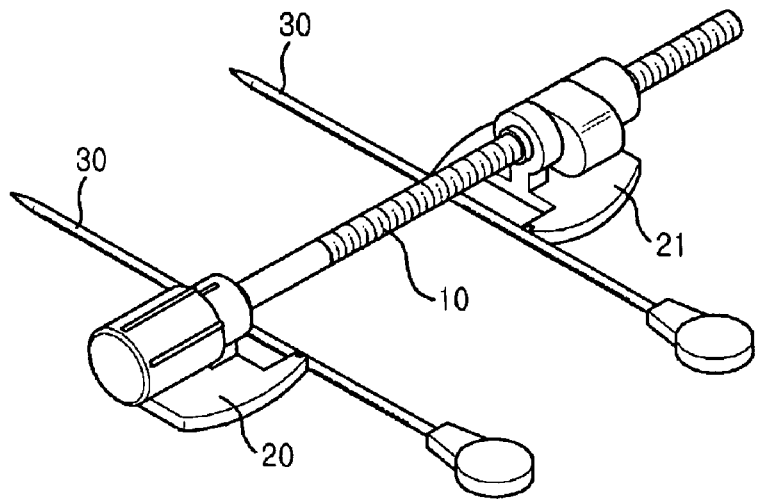
FIG. 1 is a perspective view illustrating a conventional wound closure assisting apparatus.
Figure 2:
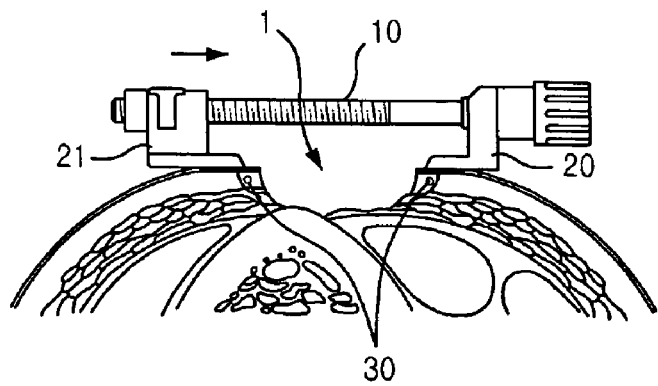
FIGS. 2 and 3 are side sectional views depicting a process of using the conventional wound closure assisting apparatus.
Figure 3:
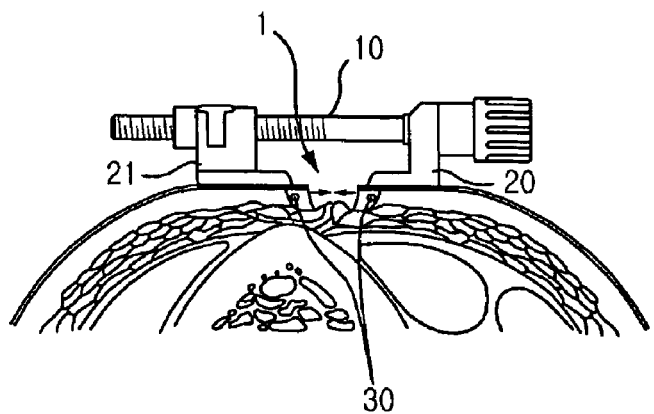

As shown in FIG. 3, when the loop suture 130, which is threaded circularly across the wide open wound 1, is pulled out of skin gradually by the pulling member 140, skin around the wide open wound 1 is stretched slowly to the middle of wound. In the end, the wide open wound 1 can be closed and wound closure can be maintained for a long time until the repaired wound gets adequate tensile strength.

Skin of human body is elastic, but it has a threshold for strain force. When loop suture is pulled to close the wide open wound 1 by the wound closure assisting and maintaining apparatus, skin is stretched but strained. Here, it is necessary to keep the strain on skin under the threshold and therefore, it is desirable to measure the strain. In order to measure the strain, a strain gauge or other devices known for strain measurement, such as a device detect the displacement using an optical sensor, may be mounted on the wound closure assisting and maintaining apparatus.

Hereinafter, another embodiment of the present invention for a strain gauging unit or a buffering unit is described.

Figure 6:
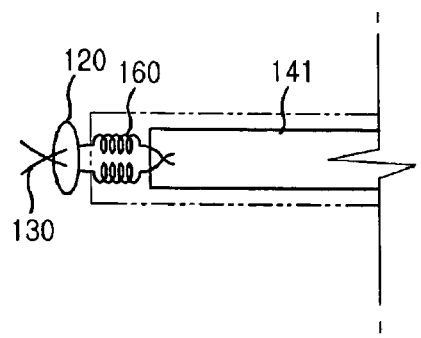
FIG. 6 is a cross-sectional view illustrating a strain gauging unit with a coil spring in a housing unit of the wound closure assisting and maintaining apparatus in accordance with the embodiment of the present invention.
Figure 7:
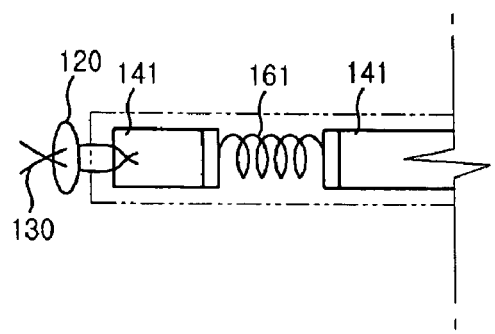
FIG. 7 is a cross-sectional view illustrating a buffering unit with a coil spring in the housing unit of the wound closure assisting and maintaining apparatus in accordance with the embodiment of the present invention.

FIGS. 6 and 7 are cross-sectional views illustrating an elastic member as a strain gauging unit and a buffering unit in a housing member of the wound closure assisting and maintaining apparatus in accordance with another embodiment of the present invention.

Referring to the FIG. 6, the elastic member 160 is equipped between a tightening member 120 and the pulling member 141. In FIG. 6, a coil spring is used as the elastic member 160.

Also, FIG. 7 shows another embodiment of the present invention having the elastic member 161 installed between half divided pulling member 141. As shown in FIG. 7, the pulling member is splitted into two pieces and the elastic member 161 is inserted between two portions of splitted pulling members 141. Also, the elastic member 161 can be inserted in the middle of the housing member 110, in addition to the previously described sites between the tightening member 120 and the pulling member 141 and between two portions of divided pulling member 141.

When the elastic member is strained, it is extended in proportion to the strain based on an elastic coefficient. Therefore, a level of strain can be measured by the extended length of the elastic member. Therefore, the elastic member can be used as a strain gauging unit In FIG. 6, the level of strain loaded on the thread loop suture 130 can be measured by extended length of the elastic member 160. In FIG. 7, the strain on the thread loop suture 130 can be measured by extended length of the elastic member 161. In order to prevent breakage of the loop suture 130 by too much strain on it, the loop suture 130 should have a yielding strength higher than that of skin. Today, most commercially available suture materials are known to suffice these criteria. It is skin that is vulnerable to too much strain.

Although the strain on skin and the loop suture are not exactly the same, they are in proportion to each other. Therefore, if the strain of loop suture can be measured, it is desirable to form a table of allowable skin strain levels for variable body areas to treat the patient safely within limit of the mechanical strength of skin. In addition to mechanical limitation, skin has another biological limitation of blood supply. Skin should have its own blood supply to survive. The capillary in skin will be closed if it is exposed to the excessive strain which exceeds the minimal intraluminal pressure required for patency. So, table of allowable skin strain levels should consider the minimal intraluminal pressure for capillary.

In FIGS. 6 and 7, the elastic member is installed between the tightening member 120 and the pulling member 141 and between two portions of divided pulling member 141 respectively for the strain measurement and buffering. Also, the elastic member can be inserted in the middle of the housing member 110 to function as a strain measurer and buffer, when the wound closure assisting and maintaining apparatus is attached to the patient.

Figure 8:
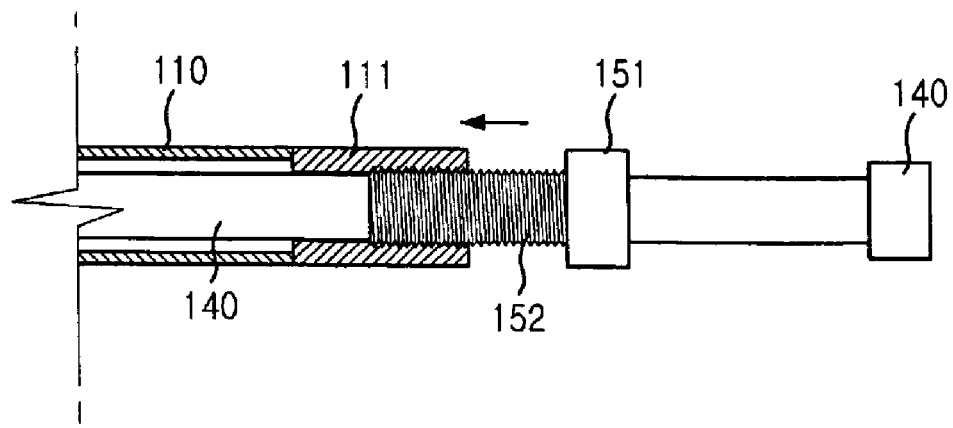
FIG. 8 is a cross-sectional view showing a wound closure assisting and maintaining apparatus with a loosening unit consists of a male screw and a female screw on one end of the housing unit of the wound closure assisting and maintaining apparatus in accordance with the embodiment of the present invention.

FIG. 8 shows another embodiment of the present invention having a loosening unit for releasing a loop suture 130, when the loop suture 130 is tightened too much more than the yielding strength of skin. In FIG. 8, the wound closure assisting and maintaining apparatus includes a female screw 111 formed at one end of the housing member 110 and a loosening bolt 152 formed on the locking member 151.

If the strain measuring unit shows that the loop suture 130 is over tightened, or a doctor perceives it, the pulling member 140 needs to be pushed back to loosen the overly tightened loop suture thread. However, since it is desirable for the pulling member 140 to move in one direction only, the overtightened loop suture can be loosened by backward movement of the locking member 151 using the screw opening 111 and the bolt 152.

Figure 9:
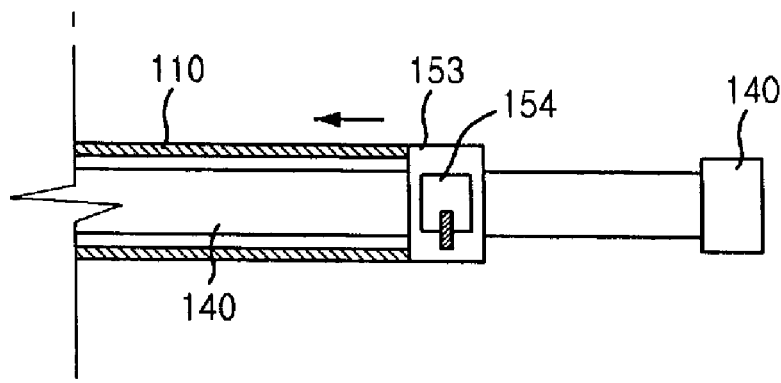
FIG. 9 shows a structure of another loosening unit equipped in accordance with another embodiment of the present invention.

FIG. 9 shows a structure of another loosening unit equipped in accordance with another embodiment of the present invention. Referring to FIG. 9, the wound closure assisting and maintaining apparatus includes a cover 154 on the locking member 153. The cover 154 has a saw tooth (not shown) attached at inside of it. The locking member 153 locks the pulling member 140 by engagement between the saw tooth of cover and another saw tooth on surface of the pulling member 140. When opening the cover 152, the saw tooth of cover is disengaged from another saw tooth of the pulling member and therefore, the locked pulling member 140 is released. That is, when the loop suture is overtightened, it can be loosened by opening the cover and pushing the pulling member 140 in a direction opposite to the original one-way movement and fixing it at the desired position.

Figure 10:
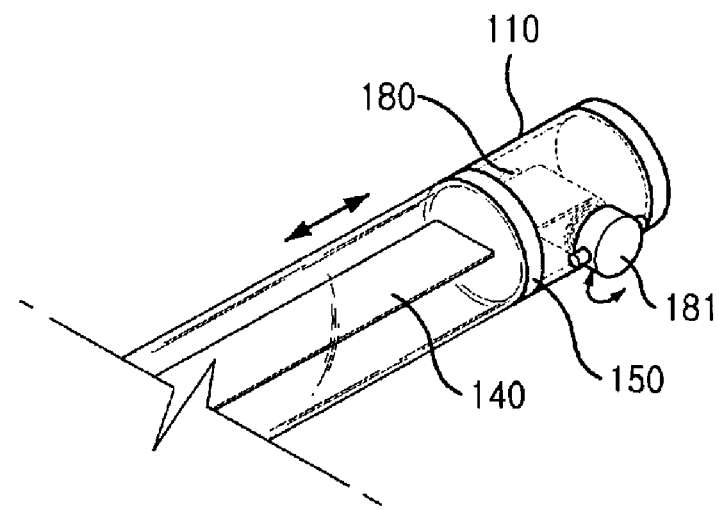
FIG. 10 shows still another loosening unit equipped in accordance with still another embodiment of the present invention.

FIG. 10 shows another loosening unit equipped in accordance with still another embodiment of the present invention.

Referring to FIG. 10, the wound closure assisting and maintaining apparatus includes a winding screw 180 and a winding screw handle 181. The winding screw handle 181 can also be external. In FIG. 10, a pulling member 140 is implanted totally inside the housing member 110 as a long flat elastic strip winded around the winding screw 180 and the pulling member 140 is fastened or loosened by turning of the winding screw handle 181 as like a film rolls in a camera. That is, when the winding screw handle 181 is turned in a direction of fastening, the winding screw winds the pulling member 140 to pull a loop suture. If the winding screw handle 181 is turned in a direction of loosening, the winding screw unwinds the pulling member 140 to release a loop suture. In addition to the function as a loosening unit, this winding screw system can reduce the overall volume of the device and discomfort of the patient.

As mentioned above, the present invention can assist and maintain the closed state of the wide open wound. To close the wound 1 completely, a large suture 130 is threaded through skin as an elongated circle across both margins of the wide open wound and tied to the pulling member 140 as a loop after passing through the tightening member 120. The pulling member 140, which holds the loop suture 130, is then pulled away from the skin slowly through the housing member 110. As the pulling member 140 and attached loop suture 130 is pulled away through the housing member 110, the pulling force is converted to the stretching force of skin around the open wound by the housing member 110 and the skin stretching force is transferred to skin through the tightening member 120. As skin around the wound is stretched gradually, the wound closure progresses. One can adjust the level of skin stretching and wound tightening according to direct visual examination of the skin, strain gauging unit, and the length of pulling on ruler scale on the pulling member 140 or housing member 110.

The position of the pulling member 140 is fixed firmly by the locking member 150 and thus, closure of the wound is maintained. Here, the skin stretching may be operated for once or several times to treat the wide open wound.

If a doctor determines that the apparatus tightens skin too much, the loop suture 130 can be released by use of the loosening unit. This way, the wound closure assisting and maintaining apparatus can be operated safely.

In accordance with the present invention, the wound closure assisting and maintaining apparatus can be applied in wounds with any surface and any shape because the wound closure assisting and maintaining apparatus uses just a suture as medium of the pulling force transferred to skin. The wound closure assisting and maintaining apparatus is applicable to any surface and any shape, but only if a loop suture placement is possible. The wound closure assisting and maintaining apparatus also can be used on any part of human body including weight bearing areas or mobile joint areas in any poor condition of the patient because it is soft, elastic, small and light and it has the impact absorbing (buffering) property.

Characteristics of the present inventions such as softness, elasticity, small volume, light weight, and impact absorbing properties make application of the present invention comfortable to the patient and maintenance of the present invention possible for a longer period of time without risk of the mechanical failure. During the initial several weeks after the operation, the strength gain of repaired wound is most rapid and directly proportional to the elapsed time. The risk of wound disruption reduces in inversely proportional to time during this critical period. Because of its longer period of application, the device does not only provide the possibility of skin stretching and wound closure but also gives an opportunity to maintain the closure until the wound strength has increased substantially.

Since the loop suture 130 penetrates across and tightens the entire wide open wound 1, the stain is distributed through the passage of loop suture evenly. Therefore, it can prevent the local concentration of too much strain on skin which may result in breakage of suture or tear of skin. The buffering mechanisms of the apparatus also contribute to the resistance against failure of wound closure. In addition, if the loosening unit is adopted, it is possible to control the level of tightening, and thus prevent the overtightening of wound.

The present application contains subject matter related to Korean patent application No. KR 2003-0042017, filed in the Korean patent office on Jun. 26, 2003, the entire contents of which being incorporated herein by reference.

While the present invention has been described with respect to certain preferred embodiments, it will be apparent to those skilled in the art that various changes and modifications may be made without departing from the spirit and scope of the invention as defined in the following claims.

The invention claimed is:

1. A suture assisting and maintaining apparatus, comprising:
    a loop suture adapted to be an elastic member configured threaded through skin around a wide open wound;
    a tightening member for gathering both ends of the threaded loop suture at one point in order to tighten the threaded loop suture and exert a pressure of wound tightening force evenly on skin;
    a pulling member for pulling the loop suture in order to tighten the threaded loop suture;
    a housing member for housing the pulling member and making the loop suture tightened by transformation of a pulling force to a wound tightening force, the tightening member being adapted to be in contact with a distal end of the housing member when said pulling member pulls the loop suture out of the skin;
    an elastic member configured to buffer the strain force loaded on the loop suture; and
    a locking member for fixing a position of the pulling member in relation to the housing member constant by moving the pulling member in one-way to maintain the tightened status.

2. The apparatus as recited in claim 1, wherein the housing member is formed of an elastic material.

3. The apparatus as recited in claim 1, wherein a scale is marked on the housing member or the tightening member.

4. The apparatus as recited in claim 1, wherein the pulling member has a first saw tooth on an outside surface of the pulling member and the locking member has a second saw tooth on an inside surface of the locking member in reverse form of the first saw tooth on the pulling member to check the movement of the pulling member as one-way and to prevent slippage of the pulling member in an opposite direction after pulling by engagement between the saw teeth of the pulling member and the second saw tooth of the locking member.

5. The apparatus as recited in claim 4, further including a loosening means with a cover having a third saw tooth on an inside surface of the cover, wherein the third saw teeth is engaged or disengaged with the first saw tooth on the pulling member by opening the cover from the loosening means in order to adjust the position of the pulling member.

6. The apparatus as recited in claim 1, further comprising a strain gauging means for measuring a strain force of the loop suture.

7. The apparatus as recited in claim 6, wherein the strain gauging means is formed of an elastic material and connected to the loop suture.

8. The apparatus as recited in claim 1, wherein the elastic member is inserted into a predetermined position of the pulling member.

9. The apparatus as recited in claim 8, wherein the elastic member is a coil spring.

10. The apparatus as recited in claim 1, wherein the elastic member is inserted into a predetermined position of the housing member.

11. The apparatus as recited in claim 10, wherein the elastic member is a coil spring.

12. The apparatus as recited in claim 1, further comprising a loosening means for releasing the over-tightened loop suture by adjusting the position of the pulling member.

13. The apparatus as recited in claim 12, wherein the loosening means includes:
    a female nut formed at one end of the housing member; and
    a loosening bolt formed on the locking member.

14. The apparatus as recited in claim 12, wherein the loosening means includes:
    a winding screw for winding the pulling member in order to tighten the loop suture; and
    a winding screw handle for being connected to the winding screw and providing a torque to wind the pulling member.

15. The apparatus as recited in claim 1, wherein said loop suture is a multiple punctured purse-string type loop suture.

16. The apparatus as recited in claim 1, wherein said tightening member defines an interface between skin and the apparatus for distribution and buffering of even-pressure.

* * * * *